United States Patent
Ohtsuki et al.

(10) Patent No.: US 6,638,224 B2
(45) Date of Patent: Oct. 28, 2003

(54) ECHO IMAGE FORMING APPARATUS AND METHOD

(76) Inventors: Shigeo Ohtsuki, 12-15, Yokoyama 2-chome, Sagamihara-shi, Kanagawa (JP); Motonao Tanaka, 4-26, Kunimi 4-chome, Aoba-ku, Sendai-shi, Miyagi (JP)

(*) Notice: Subject to any disclaimer, the term of this patent is extended or adjusted under 35 U.S.C. 154(b) by 0 days.

(21) Appl. No.: 09/859,468

(22) Filed: May 18, 2001

(65) Prior Publication Data

US 2001/0032512 A1 Oct. 25, 2001

(51) Int. Cl.[7] ................................................ A61B 8/00
(52) U.S. Cl. ........................................ 600/443; 600/437
(58) Field of Search ............................ 600/437–472; 382/181, 192–197

(56) References Cited

U.S. PATENT DOCUMENTS

| | | | | |
|---|---|---|---|---|
| 3,156,110 A | * | 11/1964 | Clynes .......................... | 73/628 |
| 4,228,804 A | * | 10/1980 | Holasek et al. ............... | 600/443 |
| 4,485,821 A | * | 12/1984 | Iinuma ......................... | 600/455 |
| 4,561,019 A | * | 12/1985 | Lizzi et al. ................... | 348/163 |
| 4,646,748 A | | 3/1987 | Fujii et al. | |
| 4,750,366 A | | 6/1988 | Nicolas | |
| 4,858,124 A | * | 8/1989 | Lizzi et al. ................... | 600/443 |
| 5,361,767 A | * | 11/1994 | Yukov .......................... | 600/442 |
| 6,072,885 A | * | 6/2000 | Stockham et al. ............. | 381/312 |
| 6,438,258 B1 | * | 8/2002 | Brock-Fisher et al. ....... | 382/128 |

\* cited by examiner

Primary Examiner—Marvin M. Lateef
Assistant Examiner—William C Jung
(74) Attorney, Agent, or Firm—Dickstein Shapiro Morin & Oshinsky LLP

(57) ABSTRACT

A probe 10 transmits an ultrasonic pulse of a wide band, and detects its echo to generate a reception signal. The reception signals are respectively filtered by three filter parts (14a to 14c) of different passing bands. Outputs of the respective filter parts (14a to 14c) are signal components of a narrow band, and speckle components (interference components by a fine structure) appear conspicuously. Outputs of the respective filter parts (14a to 14c) are detected, and the detection outputs are set respectively as each color signal of R, G and B, and are composed by an image composition part (20), whereby a speckle part is displayed by coloring in R, G or B. As a tissue boundary part is high in a signal level in any band, it is displayed in a whitish color by composition.

3 Claims, 3 Drawing Sheets

ECHO IMAGE FORMING APPARATUS AND METHOD

BACKGROUND OF THE INVENTION

1. Field of the Invention

The present invention relates to an apparatus and method for imaging an object using echoes of observation waves such as an ultrasonic image diagnosis, a weather observation radar, or the like.

2. Description of the Related Arts

An ultrasonic diagnostic device is widely spread as a device for observing a state of a structure, a movement, and the like of an organism tissue interior in non-invasion. The ultrasonic diagnostic device generically transmits ultrasonic waves into an organism tissue and receives echoes (reflected waves) reflected from the organism tissue interior, and implements a signal process with respect to this echo signal to extract various pieces of useful information, and images it to display. As typical displays, one of them is a B mode tomographic display in which ultrasonic beams are scanned to reconstruct the echo signal according to the scan pattern to display a two-dimensional tomogram, and is also a Doppler tomographic display in which a Doppler component of the echo signal is extracted to display a two-dimensional distribution of a speed of a moving body.

As is commonly known, ultrasonic waves are reflected on an interface between media of different acoustic impedances, thereby forming an echo signal. Accordingly, the most conspicuous echo signal is reflected from an interface between internal organs, an interface between the internal organ and its interior or a surrounding liquid, or the like, and a shape of the internal organ, etc. can be read from the B mode image, etc. Furthermore, there are many cases that the acoustic impedance is different between a normal region and a lesion region even in the same internal organ, and from this nature, it is possible to find out the lesion region from the B mode image, etc.

The organism tissue as an object of the ultrasonic diagnosis device has a finer structure than wavelength of ultrasonic waves for use in a diagnosis. Accordingly, not only a definite echo from the interface but also a scattered echo due to the fine structure of the internal organ and the other soft tissue interior are returned. The scattered echoes due to these fine structures interfere with each other, so that a so-called speckle pattern consequently appears in this ultrasonic image.

Conventionally, such the speckle pattern is considered to be an artifact, and some devices are taken so as to produce the speckle pattern as little as possible. Lately, it is possible to make very acute a transmission ultrasonic pulse (namely a wide band), and such the expansion of a pulse band is useful greatly for a reduction in the speckle.

It is difficult to find out the speckle because the speckle itself is an image which appears as a result of interference with the echo from each part of the fine structure, and the speckle is same with the echo from a boundary surface between the normal tissue and the lesion region in view of a signal. Namely, at a level of the signal process, it is possible to distinguish between the signal components of the speckle and the echo signal from the boundary surface. Accordingly, a judgment whether a noticeable part of the image is a part of a large structure of the boundary surface, etc. or the speckle is entrusted to one (viewpoint) of an observer who looks at it. In many cases, the judgment whether or not the speckle is delicate, and only the sufficiently experienced observer could judge it accurately.

In the above description, such a problem was designated that the speckle is captured as negative information, and the negative information cannot be distinguished in view of a signal from positive information of the boundary surface of the lesion region, etc., and there is a case where it is difficult to distinguish in view of images. On the other hand, if considering that the speckle is attributable to the fine structure of about wavelength of the tissue, it is considered that the speckle pattern is captured as the positive information reflecting the fine structure of the tissue, and is positively put to some use in the diagnosis.

However, even in this case, such a problem is confronted that the speckle cannot be distinguished from the echo of the boundary surface in view of the signal.

If the speckle part can be imaged by distinguishing it from the boundary surface of a large structure in any shape, the observer can come to recognize the speckle and a part of the large structure by distinguishing, but there did not conventionally exist an imaging apparatus or method proposed from such a viewpoint.

In the above description, the prior art and its problems were explained exemplifying an ultrasonic diagnostic field, but the same problem occurs in a weather observation radar, etc.

SUMMARY OF THE INVENTION

The present invention was conceived to solve such the problems, and in the apparatus and method for imaging an echo of observation waves, it is an object of the present invention to provide a technique for distinguishing a speckle pattern by a fine structure of a size of about wavelength of the observation waves from a large structure to image. Furthermore, it is an object of the present invention to extract characteristics of the fine structure.

In order to attain the above objects, this echo image forming apparatus according to the present invention comprises: a wave transmitter for transmitting an observation wave pulse of a wide band; a wave receiver for receiving an echo of the observation wave pulse transmitted to generate a reception signal; a filter for extracting signal components of a plurality of different frequencies predetermined from the reception signal obtained by the wave receiver; and a display device for imaging separately respectively the signal components of each frequency extracted by the filter and displaying images corresponding to resultant frequencies mutually relating to each other.

Herein, as the observation waves, various waves such as ultrasonic waves, electromagnetic waves, or the like can be used in correspondence with objects or targets of observation.

With this structure, the signal components of the plurality of frequencies predetermined are extracted from the reception signal of the wide band by use of the filter. The speckle patterns by the fine structure of about wavelength in correspondence with the corresponding frequency emerge respectively in each extracted frequency component. Conventionally, the expansion of bands of the transmission waves decreases influences of the speckle, but according to the present invention, components of a specified frequency are daringly fetched out from the reception signal of the wide band, thereby making prominent the speckle. However, when the signal of the extracted single frequency is merely imaged, as described already, it is impossible to distinguish the image part representing the boundary surface of the large structure from the speckle.

Then, according to the present invention, the signal components of the plurality of frequencies are extracted from the wide band reception signal, and imaging is performed in each of respective signal components, and they are displayed mutually relating to each other.

The speckle is generated due to interference between the scattered waves in the fine structure, and as is commonly known, the interference depends on a relationship between a wavelength and an interval of a wave source (in this case, an interval of the fine structure). Accordingly, if a frequency of a signal differs (namely, wavelength), the looking speckle differs. Namely, when the speckle is seen in the signal of a certain frequency, it is considered that the speckle part has the fine structure of the interval in correspondence with the frequency (wavelength), and this part does not generate interference by the observation waves of the frequency differing there from. Accordingly, it occurs that, if a speckle, it shows up in the image of the signal component of a certain frequency, and it does not show up in the image of the signal component of another frequency. On the contrary, the echo from the boundary surface shows up in the signal components of any frequencies.

Accordingly, if displaying respective images generated from the signal components of the plurality of frequencies relating to each other, it is possible to judge that the image emerging in all images is the boundary surface, and it is possible to judge that the image emerging only in any one image is a speckle of the fine structure. Furthermore, in the speckle part, the interval of the fine structure of the part can be assumed according to appearance in which frequency's image. Namely, according to the present invention, in the fine structure, it is possible to obtain quantitative information which has not been obtained in the prior art.

There may be various methods for displaying the images in correspondence with each frequency relating to each other, and as a preferred embodiment, there is a method in which the images in correspondence with each frequency are assorted by coloring, respectively, and are displayed by overlaying. By such overlaying, the boundary part between the speckle part in correspondence with each frequency and the large structure can be confirmed at a glance. Furthermore, the interval of the fine structure in each part can be discriminated by assortment by coloring.

In one aspect of the invention, a system for setting the frequency extracted by a filter as three types and corresponding the signal components of each frequency to each color of the three primary colors of an output device (a display or a printer device) is preferred from several viewpoints. For example, in the part of the boundary surface, all levels of the signal components of three frequencies are increased, but on the contrary, in the part of the fine structure, only a level of the signal component of a frequency matching the interval of the structure is increased. Accordingly, in the output device of a color increasing mixture system such as a CRT display, etc., as all levels of the three primary colors (for example RGB) in the part of the boundary surface are increased, a display is whitish, and the part of the fine structure is displayed in a color close to the primary color. Accordingly, it becomes easy to distinguish the fine structure and the boundary surface in displaying. In particular, when displayed as the B mode tomographic image, it is possible to grasp at a glance which part of respective tomographic surfaces is the boundary surface and which part has which degree of fineness in the fine structure. Furthermore, when used as a signal of the primary color (for example, cyan, magenta, yellow) of the output device of a color decreasing mixture system such as a printer, etc., as the signal levels of all the primary colors are high in the part of the boundary surface, it is blackish, and the part of the fine structure is expressed in vivid coloring. Accordingly, it is possible to express with the part of the fine structure outstanding.

Furthermore, in another aspect of the invention, a system for performing brightness modulation in the images at intensity of the reception signal of an original wide band is considered. According to this, the display reflecting the fine structure according to the present invention is possible by overlaying on the common image display in the prior art. For example, when the B mode tomogaphic image is formed by this system, the speckle pattern having a color representing the fine structure is overlapped on the tomographic image (monochroic image) having a superior resolution, and it is easy to specify a location of each fine structure.

Furthermore, in yet another aspect of the invention, the echo image forming apparatus comprises: a wave transmitter for transmitting observation waves of a plurality of different frequencies from the substantially same position; a wave receiver for receiving an echo of the observation waves of each frequency of the transmitted waves to generate a reception signal of each of respective frequencies; and a display device for imaging separately respectively the reception signal of each of the respective frequencies to display an image corresponding to each resultant frequency mutually relating to each other.

In this aspect, the plurality of observation waves having different frequencies are transmitted and the reception signal of each frequency is imaged, and the images are displayed mutually relating to each other. According to such system also, the same result as in the above system for extracting the signal components of the plurality of frequencies from the echo of the transmission observation waves of the wide band to image can be obtained.

Incidentally, in the above respective aspects, the images are formed respectively from the signal of the plurality of different "frequencies," and here the "frequency" follows an ideal sense in a principle, and actually this "frequency" is a frequency band having a width to some degree. Accordingly, in case of the plurality of different frequencies, it is desired to understand that they designate the plurality of frequency bands which can be made a sharp distinction significantly.

DESCRIPTION OF THE PREFERRED EMBODIMENT

An embodiment of the present invention will now be described with reference to the drawings.

Figure 1:
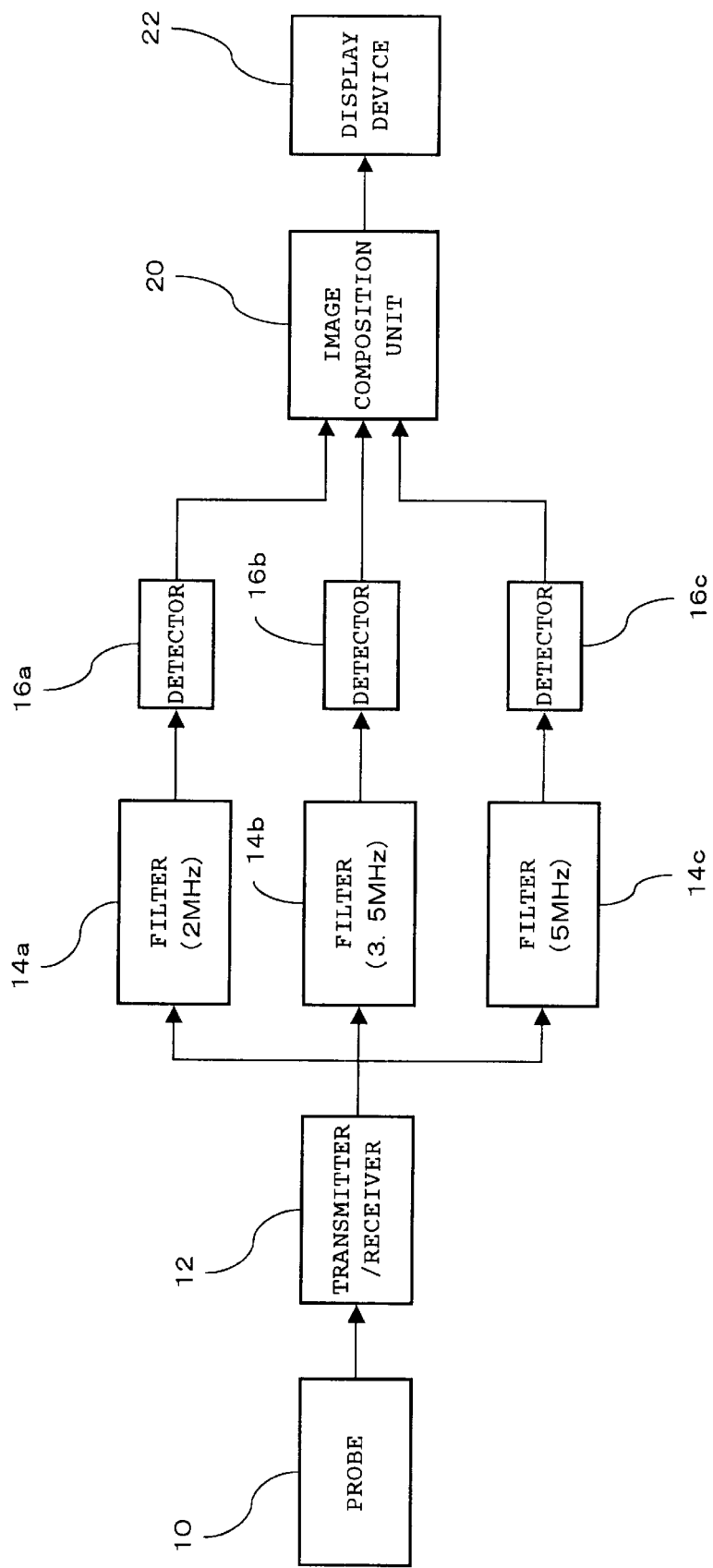
FIG. 1 is a schematic functional block diagram of an apparatus according to an embodiment.

FIG. 1 is a functional block diagram showing a schematic configuration of an image forming mechanism according to the present invention. This example in FIG. 1 is the image forming mechanism adapted to an ultrasonic diagnosis device, and illustrates mainly a part relating to a reception.

A probe 10 excites an ultrasonic transducer according to a drive pulse from a transmitter/receiver 12, and generates a transmission ultrasonic pulse to output it, and receives echoes (reflected waves) from an object of an organism, etc., and converts them to electrical reception signals. The transmitted ultrasonic pulse is a pulse of a very wide band and a short pulse width, and the echo from the object becomes a wide band signal. In case of the ultrasonic diagnosis device for forming a B mode tomographic image, the probe 10 typically comprises a transducer array of an electronic scan system.

The transmitter/receiver 12 controls an ultrasonic transmission from the probe 10, and also processes the reception signal obtained by the transducer array of the probe 10 for an amplification or the like. In case of an electronic scan, this transmitter/receiver 12 performs a phasing addition processing for forming beams. The reception signal output from the transmitter/receiver 12 is branched to three paths, and is in parallel input into three filter parts 14a, 14b, 14c.

Figure 2:
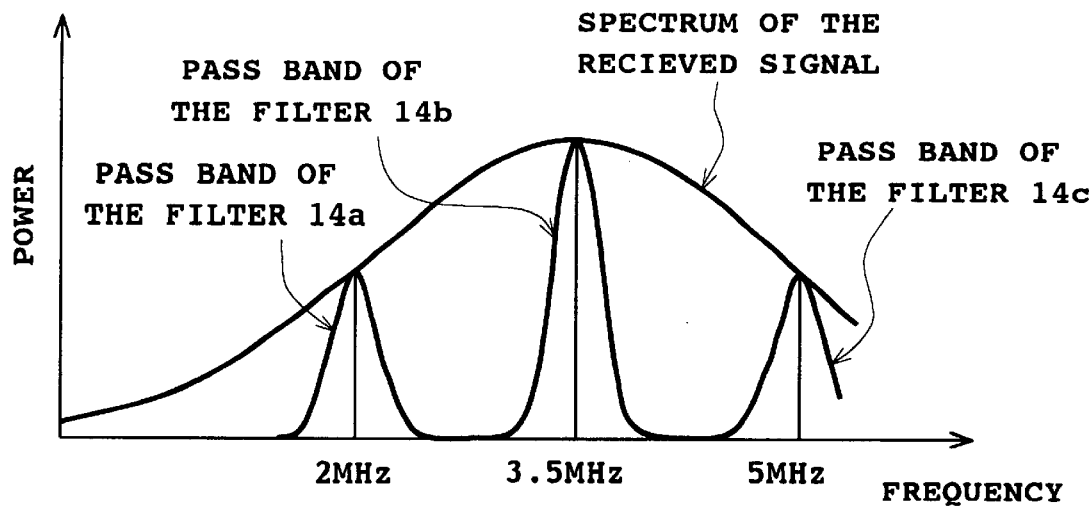
FIG. 2 is a graphic representation showing a relationship between a spectrum of a reception signal of a wide band and a passing band of each filter part.

Each of the filter 14a to 14c is a band path filter of a narrow band in which a passing band is mutually different. FIG. 2 is a graphic representation for explaining a relationship between a spectrum of the reception signal and the passing band of each filter. As shown in FIG. 2, the filters 14a and 14b are band path filters of a passing band width about a few tens to a few hundreds KHz, respectively, and the respective passing bands are established so as not to overlap each other basically. As a transmission path is a sufficient wide band, the reception signal becomes a wide band signal, and each of the filter parts 14a to 14c fetches out components of a plurality of different frequency bands, respectively. In this example, a central frequency of the filter 14a is set to be 2 MHz, and the central frequency of the filter 14b is set to be 3.5 MHz, and the central frequency of the filter 14c is set to be 5 MHz.

Outputs of the filter parts 14a to 14c are detected by detector 16a to 16c, respectively. Incidentally, a logarithmic amplifier is provided just before the detector 16a to 16c in the same manner as a general B mode tomographic image forming mechanism, but as this point is merely nothing but a background item of the present invention, it is omitted in FIG. 2. Detection outputs of the respective detector 16a to 16c are input to an image composition unit 20.

The image composition unit 20 uses an output of the detection part 16a as a R (red) signal, an output of the detection part 16b as a G (green) signal, and an output of the detection part 16c as a B (blue) signal, to constitute a color image. This process forms the R image from the output of the detection part 16a, and forms the G image from the output of the detection part 16b, and forms the B image from the output of the detection part 16c, and it is possible to capture this process as a process for overlaying and composing these images of the three primary colors.

This R image includes information of the boundary surface of the object tissue as well as a speckle pattern corresponding to a signal component of a narrow band of the central frequency 2 MHz.

Figure 3:
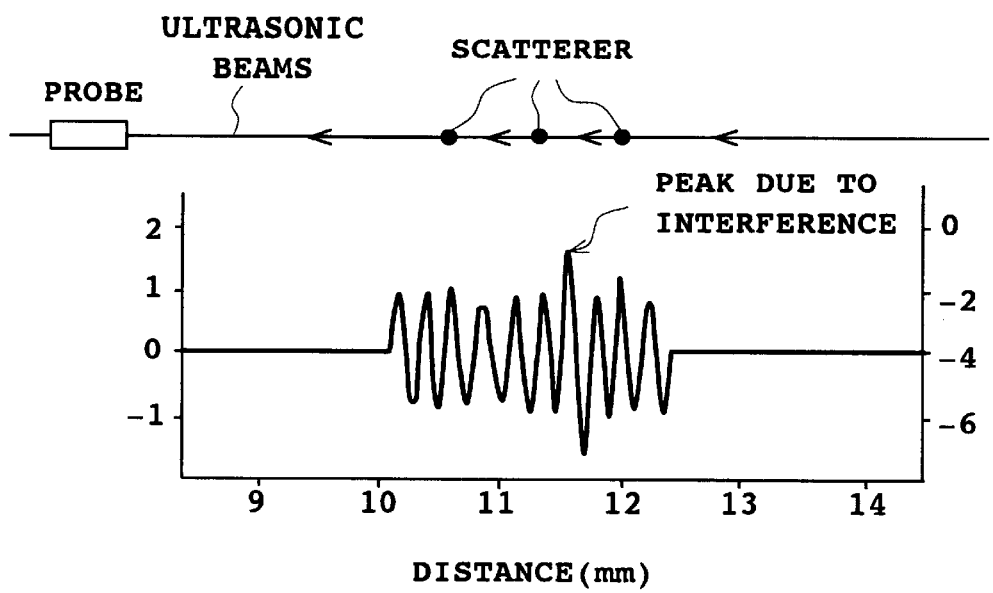
FIG. 3 is a graphic representation for explaining interference by a scatterer at fine intervals.

Namely, as shown in FIG. 3, when beams of an ultrasonic pulse are emitted from the probe, in the case where fine scatterers are arranged in the beam path at intervals in fixed relation to representative wavelength (wavelength in correspondence with the central frequency) of such pulse, the echoes interfere with the respective scatterers, thereby intensifying or weakening the echoes. For example, when the scatterers are arranged at intervals of ½ wavelength, the echoes reinforce each other. FIG. 3 shows an example in the case where the echoes reinforce each other in this manner, and a peak due to the interference appears in the wavelength in the example of FIG. 3. Furthermore, for example, when the scatterers are arranged at intervals of ¼ wavelength, the echoes cancel each other. This is a cause of the speckle, and the narrower the band, the more this speckle is conspicuous. When the speckle pattern emerges in a narrow band signal of the central frequency 2 MHz, it is conjectured that the pattern part has the fine structure at about an interval (about 0.4 mm) corresponding to 2 MHz.

In like manner, it is conjectured that the speckle part emerging in the G image has the fine structure at an interval (about 0.2 to 0.3 mm) corresponding to 3.5 MHz, and the speckle part emerging in the B image has the fine structure at an interval (about 0.1 to 0.2 mm) corresponding to 5 MHz.

Accordingly, in the color image in which each component of these R, G and B is overlayed, the part of each fine structure having a different interval is displayed as the speckle pattern of each different color. On the other hand, as the signal is at high level even in any band component of 2, 3.5 and 5 MHz in a boundary surface of a large structure, etc., when these are overlayed to be a color close to a white, thereby distinguishing it visually from the speckle part.

The color image composed by an image composition part 20 is displayed by a display device (for example, a CRT display). An observer can understand where the fine structure is in the object tissue from this image, and can also understand to what extent the interval is in the fine structure.

Incidentally, as shown in FIG. 2, as a power of the reception signal of the passing band is different in each of the respective filters 14a to 14c, each signal level of RGB is different in even the echo from the boundary surface, for example, and there is a possibility of looking colored (however, in this case also, in the same manner, the boundary surface looks more whitish than the fine structure part). In order to avoid this, an amplifier for amplifying respectively signals at different amplification factors is provided in front steps or rear steps of the respective filters 14a to 14c, and in case of the echo from the same reflective body, the composition result of RGB has only to be an achromatic color (gray scale).

It can be said that this processing is a normalization processing of a reception signal level of each frequency band. Here, for example, in an organism, the deeper a reflection point of ultrasonic waves is, the more a spectrum of frequencies of an echo signal shifts to a low frequency side. Accordingly, in the case where a coefficient (amplification factor) for normalizing respective reception signals of 2 MHz, 3.5 MHz and 5 MHz is fixed, when a depth of the reflection point changes, it may be impossible to perform correct normalization. Then, the coefficient for normalizing the reception signal of each frequency is dynamically changed in correspondence with the depth of the reflection point (this is comprehensible according to a passing time from a transmission time point of an ultrasonic pulse), whereby such inconveniences can be dissolved. In this case, the frequency spectrum of the echo signal reflected at the depth is acquired in each of respective depths, and a correction coefficient (amplification factor) for normalizing each frequency is also acquired so that a signal power of the respective frequencies of 2 MHz, 3.5 MHz and 5 MHz in the spectrum is uniformized.

Figure 4:
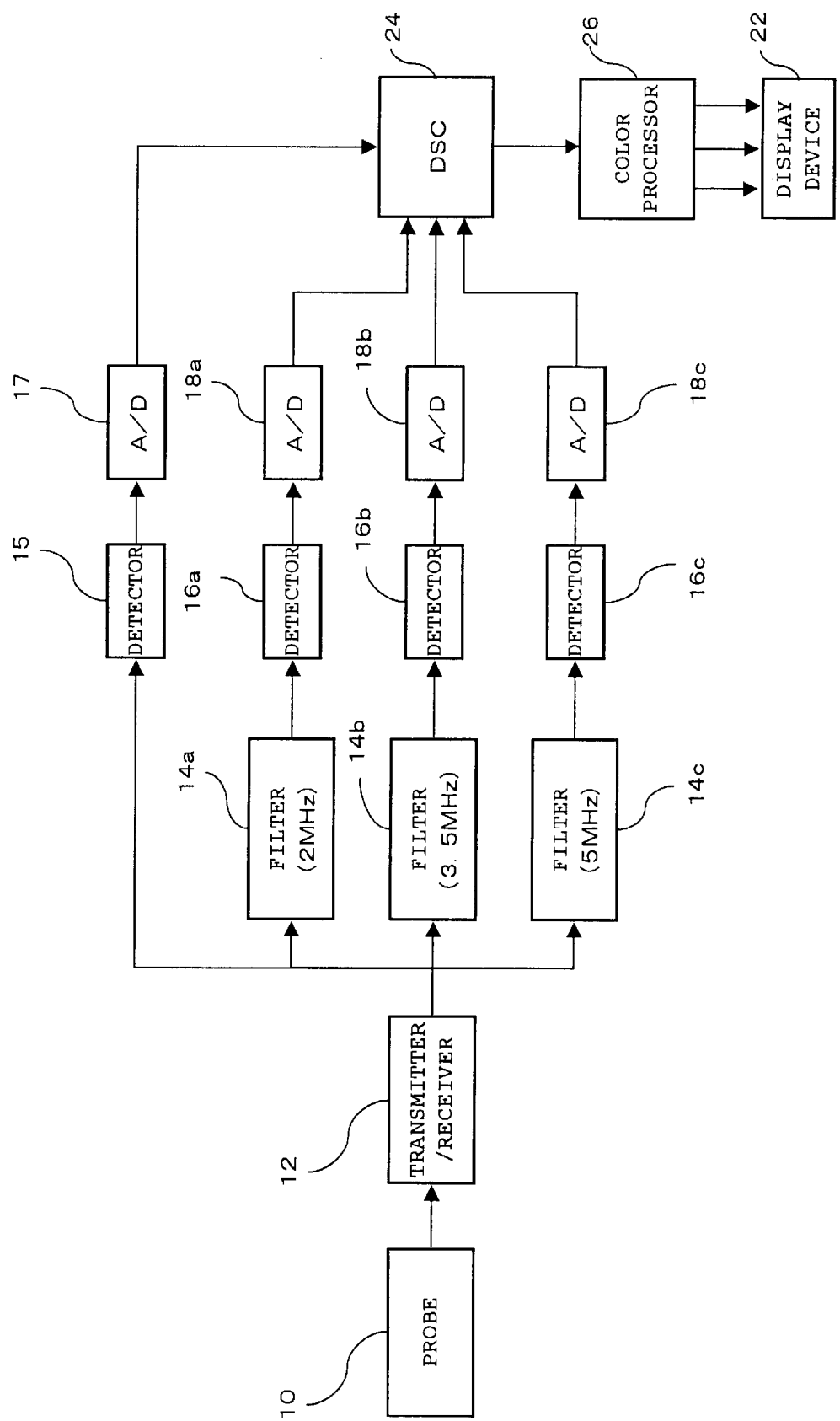
FIG. 4 is a schematic functional block diagram of an apparatus according to another embodiment of the invention.

FIG. 4 is a diagram showing an apparatus according to another aspect of the invention. In the embodiment shown in FIG. 1, as the image is formed based on the signal of the narrow band extracted by the respective filters 14a to 14c, there is a possibility that a distance resolution of the images is deteriorated. It is an object of this variation to prevent or decrease a deterioration of this distance resolution. In FIG. 4, the same reference numerals are affixed to the same structural elements as those shown in FIG. 1, and the detailed description is omitted.

This apparatus is characterized in that the color images composed from the signal components of each frequency band are modulated in brightness by all the reception signals.

That is, in this apparatus, the reception signals of the wide band output from the transmitter/receiver 12 are input to the filter parts 14a to 14c as well as a detection part 15. The reception signal of the wide band is detected by this detection part 15, and the overlayed images acquired by the above embodiment are modulated by use of this detection result.

For this reason, in this brightness modification, the detection results of each frequency band of 2 MHz, 3.5 MHz and 5 MHz are converted into digital signals by A/D converters 18a to 18c, respectively, which are input to a DSC (digital scan converter) 24. The signal level is written in the DSC 24 in each of the respective bands.

Furthermore, the detection results of the entire reception signal obtained by the detection part 15 are converted into digital data by an A/D converter 17 and also input to the DSC 24. Accordingly, the total four data of respective signal levels of 2 MHz band, 3.5 MHz band and 5 MHz band and a signal level of the entire reception signal are written into the DSC 24 in each of respective points (each point on beams more accurately) in a space (tomographic surface).

The DSC 24 scans and converts the data of the respective points so as to adapt to a display coordinate system of a display device 22. As the scan conversion process, a coordinate conversion and a process of a data interpolation, etc. with respect to a pixel position having no data are carried out.

A color processor 26 generates image signals to be supplied from the DSC 24 to the display device 22 from information of four pairs of data of the respective points (the signal levels of 2 MHz band, 3.5 MHz band and 5 MHz band and the entire reception signal). The color processor 26 captures, for example, the signal level of 2 MHz band as R components of the three primary colors of RGB, the signal level of 3.5 MHz band as G components thereof, and the signal level of 5 MHz band as B components thereof, and captures the signal level of the entire reception signal as brightness component, and composes these four components to generate the color signal for the display device 22.

The display device 22 displays images corresponding to the color signal from the color processor 26.

In this variation, information acquired in a path of the detection part 15 is substantially same as the conventional B mode tomographic image, and as this information is one formed from the reception signal of the wide band, the distance resolution is high. Accordingly, in this modification, as it is possible to obtain such the images that the color pattern of the speckle is overlayed on the tomographic image of the high distance resolution, it is possible to decrease influences of the deterioration of the distance resolution followed by the process making the narrow band in order to image the speckle in colors.

The preferred embodiment of the present invention and the variation have hereinabove been set forth by way of example.

In the above description, the display device such as CRT, etc. is exemplified as a device for outputting the images, but the images may be output from a printer, etc.

Furthermore, in the above description, the explanation was made exemplifying the image formation in the ultrasonic diagnosis device mainly, but a person having ordinary skill in the art understands that the technique of the above embodiment can adapt readily to the other echo imaging apparatus such as a weather radar, a fish finder, or the like.

Furthermore, in the above embodiment, the ultrasonic pulse of the wide band is transmitted, and a plurality of narrow band signal components were extracted from the echo signal of the wide band by the filter, and were utilized as the color signals. Instead of this, such a structure is possible that the ultrasonic pulse of the narrow band of the different frequency bands is transmitted, and the echo signal of each band is utilized as the color signal. In this case, it is necessary that the pulse of each narrow band is substantially transmitted from the same position.

Furthermore, in the above embodiment, the formation of the B mode tomographic image was described as an example, and the present invention is applicable to the other display modes such as A mode, M mode, or the like, and even in those modes, such an effect is available that it can be distinguished whether the signal is generated by interference with the fine structure or from a tissue boundary surface. For example, in the case of the A mode, when the signals of each frequency band are assorted by coloring, and the images are overlapped and displayed in synchronism with the waveforms of these signals, the signal waveforms of all colors indicate a peak in the tissue boundary part, and only the waveforms of colors of the frequency band in correspondence with the intervals of the scatterer in the fine structure part indicate the peak.

Furthermore, in the above embodiment, the three frequency bands correspond to the three primary colors, the images of the three primary colors are overlayed to form the images, but the present invention is not limited thereto, and for example, the images in each of respective frequency bands may be vertically arranged for displaying, and namely the images of each frequency band may be displayed relating to each other by another method. In the images of the A mode and M mode of the ultrasonic diagnosis apparatus, even in the above-mentioned parallel display, it is possible to distinguish between an actual image of the boundary surface and the virtual image due to the interference.

Furthermore, in the above example, respective image signals were generated from the reception signal of the respective frequencies of 2 MHz, 3.5 MHz and 5 MHz, but such combination of frequencies is persistently one example. As an example of another combination, when an ultrasonic probe of a central frequency 2.5 MHz was used, the inventors of the present invention formed images by use of the reception signal of frequencies of 2.1 MHz, 2.5 MHz and 2.9 MHz, but efficient results could be obtained. When using the reception signal of the frequency having a small difference, it is possible to decrease influences of higher harmonics. Incidentally, as it is sufficiently considered that the preferable combination of frequencies changes according to objects, it is preferable that the suitable combination of frequencies is acquired by experiments, etc. in each type of respective objects. For example, in case of an ultrasonic diagnosis, as it is considered that a fine structure of the tissue in each internal organ is different, it is desirable that the suitable combination of the frequencies has been in advance acquired in each of the respective internal organs.

Furthermore, in the above example, the reception signals of three frequency bands were used for image formation, but this is persistently one example, and a structure using two frequencies or a structure using four or more frequencies is possible.

Furthermore, in the above example, the images reflecting the fine structure of the object were formed in a real time processing from the reception signals of three frequencies, but it is justly possible that the similar processing is realized in a software processing by a computer system. In this case, the reception signal of the high frequency output from a probe is A/D-converted, and the resulting data of the high frequency reception signal are accumulated in the computer system. A frequency analysis is carried out for the data, to extract the desired signals of each frequency, and for example, R, G and B signals have only to be generated from the extracted signals.

As described above, according to the present invention, it is possible to obtain the images which can distinguish between the substantial echo components from the boundary surface and the interference components by the fine structure. In particular, the signal components of each frequency band are used as the color signal of separate color, whereby the interference components by the fine structure are displayed in color and the substantial echo components from the boundary surface are displayed in a color close to an achromatic color. Therefore, a distinction between the both is facilitated. Furthermore, the interval of the fine structure of the part can be assumed by what the color is.

What is claimed is:

1. An echo image forming apparatus adapted to distinguish an echo from a scattered echo which creates a speckle pattern in an image, comprising:

a wave transmitter for transmitting an observation wave pulse of a wide band;

a wave receiver for receiving an echo of the observation wave pulse to generate a reception signal;

a filter for extracting sign components of a plurality of different frequencies predetermined from the reception signal obtained by the wave receiver; and a display device for imaging respectively the signal components of each frequency extracted by the filter and displaying images corresponding to resultant frequencies mutually relating to each other, wherein the display device assigns a different color to the signal components of different frequency to display the obtained images of the colors by overlaying, and wherein the display device modulates the overlayed image obtained from the signal of each frequency by intensity of the reception signal as it is obtained by the wave receiver to display, thereby allowing an obtained image of a scattered echo to be distinguished from an obtained image of an echo.

2. An echo image forming apparatus according to claim 1, wherein three frequencies are used as the plurality of frequencies, and these three frequencies correspond to the three primary colors of the display device, respectively, and the display device generates an image for each of the primary colors based on the corresponding signal component, and displays the images by overlaying.

3. An echo image forming method for distinguishing an echo from a scattered echo which creates a speckle pattern in an image, comprising the steps of:

transmitting an observation wave pulse of a wide band toward an observation target region;

receiving the echo of the observation wave pulse from the observation target region to generate a reception signal;

extracting signal of the three different frequencies predetermined from the components reception signal;

for each of the signal components of each extracted frequency, generating an image of a primary color corresponding to e signal component;

overlaying the images of e primary colors to generate an output image; and displaying said output image after modulating with a power of said reception signal, thereby allowing an image of a scattered echo to be distinguished from an image of an echo.

* * * * *